United States Patent [19]

Jacquier

[11] 4,042,590
[45] Aug. 16, 1977

[54] DIAMINOPROPANOLS

[75] Inventor: Robert R. Jacquier, Montpellier, France

[73] Assignee: Centre d'Etudes Pour l'Industrie Pharmaceutique, Toulouse, France

[21] Appl. No.: 650,194

[22] Filed: Jan. 19, 1976

Related U.S. Application Data

[63] Continuation-in-part of Ser. No. 490,495, July 22, 1974, Pat. No. 3,957,789.

[30] Foreign Application Priority Data

July 24, 1973  France .................... 73.27016

[51] Int. Cl.² ............... C07D 295/08; C07D 401/12; C07D 403/12
[52] U.S. Cl. .................. 260/268 R; 260/268 PH; 260/268 H; 424/250
[58] Field of Search ......... 260/268 H, 268 R, 268 PH

[56] References Cited

U.S. PATENT DOCUMENTS 3,957,789  5/1976  Jacquier .................... 260/268 H Primary Examiner—Donald G. Daus
Assistant Examiner—Jose Tovar
Attorney, Agent, or Firm—Cushman, Darby & Cushman

[57] ABSTRACT

Hypocholesterolemic compounds of formula

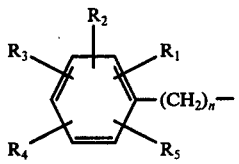
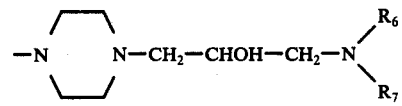

wherein $R_1$ to $R_5$, which may be the same or different, are hydrogen or halogen atoms or hydroxy, lower alkyl, lower alkoxy, trifluoromethyl, nitro, amino or sulphonylamino groups; or $R_1$ and $R_2$ together represent a methylenedioxy group, $R_6$ is a hydrogen atom or a lower alkyl group; $R_7$ is a lower alkyl, lower cycloalkyl, phenyl or lower phenylalkyl group; or wherein $R_6$ and $R_7$ when taken together with the nitrogen atom to which together with the nitrogen atom to which they are linked represent a saturated heterocyclic group having 5 to 7 ring members (optionally comprising an oxygen atom or another nitrogen atom as a second heteroatom, which latter nitrogen atom is unsubstituted or substituted by a lower alkyl group); and n is an integer of from 0 to 5; and the salts thereof.

7 Claims, No Drawings

DIAMINOPROPANOLS

This application is a continuation in part of my copending application Ser. No. 490,495 filed 7/22/74 now U.S. Pat. No. 3,957,789 granted May 18, 1976.

The present invention relates to 1,3-diamino-2-propanols, processes for the preparation thereof and the applications thereof in human and veterinary medicine.

In one aspect the invention provides 1-phenyl-piperazino -3-amino-2-propanols of formula:

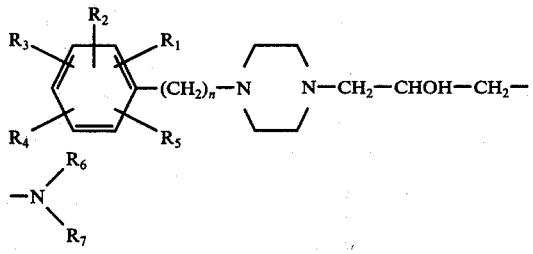

I wherein $R_1$ to $R_5$, which may be the same or different, are hydrogen or halogen atoms or hydroxy, lower alkyl, lower alkoxy, trifluoromethyl, nitro, amino or sulphonylamino groups; or $R_1$ and $R_2$ together represent a methylenedioxy group; $R_6$ is a hydogen atom or a lower alkyl group; $R_7$ is a lower alkyl, lower cycloalkyl, phenyl or lower phenylakyl group; or wherein $R_6$ and $R_7$ when taken together with the nitrogen atom to which they are linked represent a saturated heterocyclic group having 5 to 7 ring members (optionally comprising a oxygen atom or another nitrogen atom as a second heteroatom, which latter nitrogen atom is unsubstituted or substituted by a lower alkyl group); and n is an integer of from 0 to 5; and the salts thereof.

The preferred compounds are those in which at least one of $R_1$ to $R_5$ is other than hydrogen. The compounds in which $R_7$ is a cycloalkyl group having from 5 to 12, or more, preferably from 5 to 8, carbon atoms in the ring, are particularly important. The cyclohexyl-substituted compounds have been found to be very active, and likewise those where $R_3$ to $R_5$ are hydrogen atoms.

Generally, the alkyl groups or portions thereof referred to above may have up to 12, or preferably up to 6, carbon atoms, and they may be either straight or branched. Usually those groups have up to 4 carbon atoms, particularly from 1 to 3 carbon atoms.

As to the halogen atoms which may be present, chlorine, fluorine and bromine are particularly suitable. Examples of heterocyclic groups which may be formed by $R_6$ and $R_7$ and the nitrogen atom to which they are attached are the purrolidino, piperidino, piperazino and morpholino groups, of such a group substituted by an alkyl group.

The compounds of the invention may be in the form of their acid addition or quaternary ammonium salts.

Salts of the compounds of this invention are acid addition salts, such as pharmaceutically acceptable acid addition salts with inorganic acids, e.g. hydrochloric, hydrobromic, nitric, sulphuric or phosphoric acids, or with organic carboxylic acids, e.g. acetic, propionic, glycolic, malonic, succinic, maleic, hydroxymaleic, fumaric, malic, tartaric, citric glucuronic, benzoic mandelic, salicylic, 4-aminosalicylic, 2-phenoxybenzoic, 2-acetoxybenzoic, pamoic, nicotinic or isonicotinic acid, or organic sulphonic acids, e.g. methane sulphonic, ethane sulphonic, 2-hydroxy-ethane sulphonic, ethane 1,2-disulphonic, p-toluene sulphonic or naphthalene 2-sulphonic acid. Other acid addition salts are used intermediates, for example, in the preparation of other acid salts or in the purification of the free compounds, as well as for characterization and identification purposes. Salts for the latter are, for example, those with certain inorganic acids, e.g.perchloric acid, with acidic organic nitro compounds, e.g. picric, picrolonic or flavianic acid, or with metal complex acids, e.g. phosphotungstic, phosphomolybdic, chloroplatinic or Reineeke acid. Mono or poly-salts are formed depending on the number of salt forming groups present in the molecule.

Quaternary ammonium derivatives of the compounds of this invention are those with reactive esters from alcohols and strong inorganic and organic acids, particularly the lower alkyl or phenyl-lower alkyl quaternary ammonium halides, sulphates or sulphonates, such as those with lower alkyl halides, e.g. methyl, ethyl, n-propyl, isopropyl or n-butyl chloride, bromide or iodide, phenyl-lower alkyl halides, e.g. benzyl, 1 -phenylethyl or 2 -phenylethyl chloride or bromide, di-lower alkyl sulphates, e.g. dimethyl sulphate or diethyl sulphate, or lower alkyl sulphonates, e.g. methyl or ethyl methane sulphonate, ethane sulphonate or p-toluene sulphonate. Also included as the quaternary ammonium compounds are the quaternary ammonium hydroxides and other quaternary ammonium salts, in which the anion is derived from an acid other than hydrohalic, sulphuric or sulphonic acid.

The invention relates not only to the optically active diaminopropanols, but also to their racemates.

The compounds of the invention may be prepared by condensing an amine of formula AH with a compound of the formula:

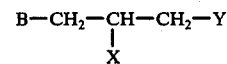

wherein A is:

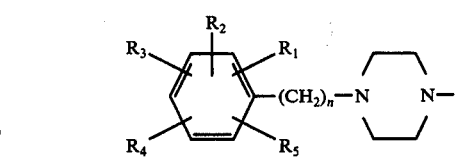

II when B is 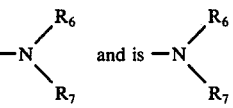 and is 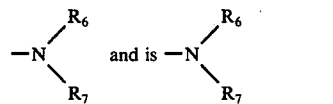

when B is a group of the formula II; Y is a halogen atom, which is advantageously chlorine, and X is hydroxy or X and Y taken together represent an oxygen atom; and wherein $R_1-R_7$ and n are as defined above.

Where Y is a halogen atom and X is a hydroxy group, the starting material may readily be prepared by reacting an epihalohydrin, in particular epichlorohydrin, with an amine B-NH. This reaction is generally performed at a temperature of between 0° and 140° C by contacting the two reagents for 1 to 18 hours depending on their nature, either in stoichiometric quantities or with an excess of the epihalohydrin.

When X and Y together represent an oxygen atom, the starting material may be prepared by alkaline treatment of the reagent in which X is a hydroxy group and Y is a halogen atom, without preliminary separation of this latter. For example a large excess of sodium hydroxide or potassium hydroxide may be used, with agitation and cooling over a period of from 5 minutes to 2 hours.

The condensation itself may be performed by refluxing the reactants for several hours, advantageously in the presence of a stoichiometric excess of the amine AH.

The addition salts of the aminopropanols of the invention with organic acids and mineral acids may be prepared by dissolving the free base in an etherified solution of the selected acid.

The following examples illustrate the invention.

EXAMPLE 1

1 -(4 -p-Fluorophenyl-piperazino)-3 -isopropylamino-2 -propanol $R_1 = R_6 = H$; $R_2 =$ fluorine; $R_7 =$ isopropyl A mixture of 11 grams of N-p-fluorophenylpiperazine and of 5.6 grams of epichlorohydrin was stirred for 12 hours at ambient temperature (during the first hours the mixture was cooled frequently such that the internal temperature did not exceed 40° C). Thus there was formed a white past-like precipitate which was heated for 16 hours under reflux with 11 grams of isopropylamine. Then the excess of isopropylamine was evaporated under vacuum, the residue taken up in 30% soda solution and extracted with ether. The etherified solution was dried out sodium sulphate; the solvent was evaporated under vacuum and the residue recrystallised from petroleum ether: m.p. 65° C (5 grams).

EXAMPLE 2

1 -Isopropylamino-3 -(4 -m-trifluoromethylphenyl-piperazino)- 2 -propanoldihydrochloride $R_1 =$ m-trifluoromethyl; $R_6 =$ isopropyl; $R_2 = R_7 = H$ A mixture of 5 grams of 5 -m-trifluoromethylphenyl-piperazine and of 2 grams of epichlorohydrin were agitated for 12 hours at ambient temperature (during the first hours the internal temperature was maintained below 40° C). The product was then heated for 16 hours under reflux with 4 grams of isopropylamine. The product was evaporated to dryness under vacuum, the residue taken up in 30% soda solution, extracted with ether, and the etherified solution dried over sodium sulphate, and the solvent evaporated. The oily residue was dissolved in anhydrous ether and treated with a stream of dry gaseous hydrochloric acid. The hydrochloride which precipitated was purified by dissolving it in absolute alcohol and reprecipitation by addition of anhydrous ether; m.p. 263° - 265° C (6 grams).

EXAMPLE 3

1 -(4 -para-Fluorophenyl-piperazino)-3 -cyclohexylamino- 2 -propanol $R_1 =$ fluorine; $R_2 = R_6 = H$; $R_7 =$ cyclohexyl A mixture of 11 grams of N-p-fluorophenylpiperazine and 5.6 grams of epichlorohydrin was agitated for 12 hours at ambient temperature, care being taken to maintain, by cooling, a temperature lower than 40° C. There was thus formed a pasty white precipitate which was heated for 16 hours under reflux with 15 grams of cyclohexylamine. Then the excess of cyclohexylamine was evaporated under vacuum, the residue taken up with 30% soda solution and extracted with ether. The etherified solution was dried over sodium sulphate; the solvent was evaporated under vacuum, and the residue recrystallised from petroleum ether. On filtration, 6.60 grams of a white powder were collected whose melting point, determined by Koeffler block, was 92° - 93° C.

EXAMPLE 4

1 -(4 -meta-Trifluoromethylphenylpiperazino)-3 -cyclohexyl- amino-2 -propanol $R_1 =$ trifluoromethyl; $R_2 = R_6 = H$; $R_7 =$ cyclohexyl A mixture of 5 grams of trifluoromethylphenylpiperazine and of 2 grams of epichlorohydrin was agitated for 12 hours at ambient temperature, whilst taking care to maintain by cooling a temperature lower than 40° C. The product was then heated for 16 hours under reflux with 7 grams of cyclohexylamine. The product was evaporated to dryness under vacuum, the residue taken up with 30% soda solution, extracted with ether, the etherified solution dried over sodium sulphate and the solvent evaporated under vacuum. After recrystallisation from petroleum ether 7.20 grams of a white powder were obtained whose melting point, determined by Koeffler block, was 55° C.

The propanols listed in Table I which follows have been prepared using the methods of the above Examples. In this Table, the first five columns give the number of the Example and the nature of the $R_1$, $R_2$, $R_6$ and $R_7$ groups, and the last column gives the physical characteristics of the compounds prepared. n is one for compound 27, and zero for the other compounds; in each case $R_3$ to $R_5$ are hydrogen atoms.

TABLE I

| EXAMPLE No. | $R_1$ | $R_2$ | $R_6$ | $R_7$ | m.p. in °C |
|---|---|---|---|---|---|
| 5 | 4-chloro | H | H | cyclohexyl | 95 |
| 6 | 4-chloro | H | methyl | cyclohexyl | 104 |
| 7 | H | H | H | cyclohexyl | 126 |
| 8 | 3-chloro | 5-chloro | H | cyclohexyl | 106 |
| 9 | 4-chloro | 3-trifluoro-methyl | H | cyclohexyl | 116 |
| 10 | 2-chloro | H | H | cyclohexyl | 75 |
| 11 | 3,4-methylenedioxy | | H | cyclohexyl | 95 |
| 12 | 3-chloro | H | H | cyclohexyl | 104 |

TABLE I-continued

| EXAMPLE No. | R₁ | R₂ | R₆ | R₇ | m.p. in °C |
|---|---|---|---|---|---|
| 13 | 3-fluoro | H | H | cyclohexyl | 72 |
| 14 | 4-chloro | H | methyl | benzyl | 58 |
| 15 | 4-chloro | H | N(R₆R₇)=piperidino | | 68–70 |
| 16 | 4-chloro | H | H | n-propyl | 78–80 |
| 17 | 4-fluoro | H | H | n-propyl | 58–60 |
| 18 | 4-chloro | H | H | t-butyl | 105 |
| 19 | 3-methoxy | H | H | isopropyl | 79 |
| 20 | 3-chloro | H | H | isopropyl | 84–85 |
| 21 | 4-methyl | H | H | isopropyl | 170–173 (2HCl . ½H₂O) |
| 22 | H | H | H | isopropyl | 56 |
| 23 | 3-tri-fluoro-methyl | H | H | isopropyl | 58–60 |
| 24 | 4-methyl | H | H | isopropyl | 64–65 |
| 25 | 3-methyl | H | H | isopropyl | 73 |
| 26 | 4-chloro | H | H | isopropyl | 67–68 |
| 27 | 3,4-methylenedioxy | | H | isopropyl | 57–60 |
| 28 | 4-fluoro | H | H | tertiary butyl | 79–80 |
| 29 | 4-methoxy | H | H | isopropyl | 73 |
| 30 | 3-trifluoro-methyl | H | H | tertiary butyl | 58–60 |

Surprisingly, the propanols according to the invention are effective hypocholesterolemiants and normolipemiants. Their activity is not accompanied by the local or general side effects caused by known anaesthetic and irritant propanol derivatives.

Hereinbelow by way of example are given the results of toxicological and pharmacological studies carried out on the propanols according to the invention.

TOXICOLOGICAL STUDY

This study has shown the low toxicity of the derivatives according to the invention.

For example, in the mouse the $LD_{50}$ at 24 hours per kg of body weight by the intravenous route is 73 mg for the compound of Example 2; 77 mg for that of Example 1; 52 mg for that of Example 3; 43 mg for that of Example 4; 37 mg for that of Example 5; 26 mg for that of Example 6; 35 mg for that of Example 7; 37 mg for that of Example 8; 49 mg for that of Example 9; 33 mg for that of Example 10; 42 mg for that of Example 11; and 38 mg for that of Example 12

PHARMACOLOGICAL STUDY

Hypocholesterolemic and normolipemic action

The compounds of the invention have been administered by gastric tubing to rats of the Wistar strain subjected to an etherogen diet for several days, the doses administered being between 12.5 mg and 100 mg per kg. The dosages used and the results obtained are shown in Tables II and III hereinafter, representing the arithmetical average over a group of five animals. Also shown are the results obtained on untreated control animals.

TABLE II

| Comparison animals | | Rats treated with the compound of Example 1 | | | Rats treated with the compound of Example 2 | | |
|---|---|---|---|---|---|---|---|
| Cholesterol g/l | lipids g/l | Doses administered mg/kg | cholesterol g/l | lipids g/l | Doses administered mg/kg | cholesterol g/l | lipid g/l |
| 0.81 | 3.65 | 12.5 | 0.64 | 2.76 | 12.5 | 0.75 | 2.97 |
| 0.96 | 3.43 | 50.0 | 0.50 | 2.53 | 50.0 | 0.58 | 2.38 |
| 0.92 | 3.75 | 100.0 | 0.38 | 1.67 | 100.0 | 0.43 | 1.92 |

TABLE III

| Comparison animals | | Rats treated with the compound of Example 4 | | | Rats treated with the compound of Example 10 | | |
|---|---|---|---|---|---|---|---|
| Cholesterol g/l | lipids g/l | Doses administered mg/kg | cholesterol g/l | lipids g/l | Doses administered mg/kg | cholesterol g/l | lipids g/l |
| 0.85 | 3.45 | 12.5 | 0.57 | 2.58 | 12.5 | 0.53 | 2.65 |
| 0.91 | 3.52 | 50.0 | 0.45 | 2.36 | 50.0 | 0.46 | 2.18 |
| 0.88 | 3.68 | 100.0 | 0.33 | 1.84 | 100.0 | 0.36 | 1.72 |

An examination of these Tables shows the particularly important action of the compounds of the invention, not only on the cholesterol level but also on that of the blood lipids.

The propanols of the invention likewise possess a slight anti-inflammatory and antalgic activity; these properties having been shown in test animals by the carrageenin test on the one hand and by the acetic acid test on the other hand.

As will be apparent from the above, the pharmaceutical compositions of the invention comprising the aforementioned propanols or their non-toxic salts are particularly indicated for hypercholesterolemias and hyperlipidemias, cholesterolemia and lipemia being clearly improved after treatment.

For these indications, the compositions of the invention may be presented for oral administration in the form of tablets, pills or coated tablets, capsules or syrups. They may also be presented in the form of suppositories for rectal administration or in the form of an injectable solution for parenteral administration.

The compositions may be in dosage unit form, each unit advantageously containing from 50 mg to 400 mg of the active compound together with, for example, 100 to 500 mg of excipient; the doses administrable per 24 hours may vary from 100 mg to 1 g according to the severity of the affliction treated.

For instance a compound according to the invention of the formula:

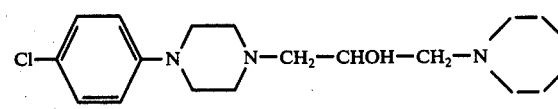

wherein N ($R_6$ $R_7$) is azepino and which is a creamy white powder (melting point 46° C), may be used as capsules. each containing 100 mg of the active compound together with 250 mg of excipient.

I claim

1. A compound of the formula:

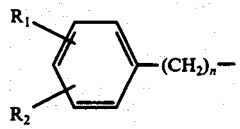

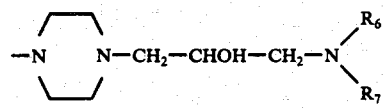

wherein $R_1$ and $R_2$ are hydrogen, fluorine, chlorine, methyl, methoxy, trifluoromethyl or, where taken together, represent a methylenedioxy group, and $$\diagdown N \diagup \begin{matrix} R_6 \\ \\ R_7 \end{matrix}$$

represents piperidino or azepino, N is zero or one, or the pharmaceutically acceptable acid addition and quaternary ammonium salts thereof.

2. A compound as claimed in claim 1, wherein $R_1$ is chlorine.

3. A compound as claimed in claim 1, wherein $R_2$ is hydrogen.

4. A compound as claimed in claim 1, wherein N($R_6$ $R_7$) is piperidino.

5. The compound of claim 1 wherein $R_1$ is chlorine, $R_2$ is H and N($R_6$ $R_7$) is piperidino.

6. A compound as claimed in claim 1 wherein N($R_6$ $R_7$) is azepino.

7. The compound of claim 6, wherein $R_1$ is chlorine and $R_2$ is hydrogen.

* * * * *